(12) United States Patent
Weissman

(10) Patent No.: US 7,595,417 B2
(45) Date of Patent: Sep. 29, 2009

(54) CYANATION OF AROMATIC HALIDES

(75) Inventor: Steven A. Weissman, Short Hills, NJ (US)

(73) Assignee: Merck & Co., Inc., Rahway, NJ (US)

( * ) Notice: Subject to any disclaimer, the term of this patent is extended or adjusted under 35 U.S.C. 154(b) by 710 days.

(21) Appl. No.: 11/272,614

(22) Filed: Nov. 14, 2005

(65) Prior Publication Data

US 2006/0106223 A1    May 18, 2006

Related U.S. Application Data

(60) Provisional application No. 60/627,676, filed on Nov. 12, 2004.

(51) Int. Cl.
 *C07C 253/12* (2006.01)
(52) U.S. Cl. ...................... 558/342; 558/343
(58) Field of Classification Search ............... 558/342, 558/343
 See application file for complete search history.

(56) References Cited

U.S. PATENT DOCUMENTS 4,211,721 A * 7/1980 Cotter ..................... 558/343

OTHER PUBLICATIONS

Beletskaya et al., Chem. Rev., vol. 100 (2000), pp. 3009-3066, "The Heck reaction as a sharpening stone of palladium catalysis".
Reetz et al., Tet. Letters, vol. 39 (1998), pp. 8449-8452, "A highly active phosphine-free catalyst system for Heck reactions of aryl bromides".
Li et al., Org. Letters, vol. 6 (2004), pp. 2809-2811, "Dabco as an inexpensive and highly efficient ligand for palladium-catalyzed Suzuzi-Miyaura cross-coupling reaction".
Urgaonkar et al., J. Org. Chem., vol. 69 (2004), pp. 5752-5755, "Ligand-, copper-, and amine-free Sonogashira reaction of aryl iodides and bromides with terminal alkynes".
de Vries et al., Eur. J. Org. Chem. (2003), pp. 799-811, "The power of high-throughput experimentation in homogeneous catalysis research for fine chemicals".
de Vries et al., Org. Letters, vol. 5 (2003), pp. 3285-3288, "Homeopathic ligand-free palladium as a catalyst in the Heck reaction . . . ".
Schareina et al., Chem. Commun., vol. 12 (2004), pp. 1388-1389, "Potassium hexacyanoferrate (II)—a new cyanating agent for the palladium-catalyzed cyanation of aryl halides".
Sundermeier et al., Angew. Chem. Int. Ed., vol. 42 (2003), pp. 1661-1664, "A convenient procedure the palladium-catalyzed cyanation of aryl halides".
Sundermeier et al., J. of Organomet. Chem., vol. 684 (2003), pp. 50-55, "A convenient and efficient procedure for the palladium-catalyzed cyanation of aryl halides using trimethylsilylcyanide".
Yang et al., Org. Letters, vol. 6 (2004), pp. 2837-2840, "Palladium-catalyzed cyanation of aryl bromides promoted by low-level organotin compounds".
Okano et al., Synlett (1998), pp. 243-244, "Catalytic cyanation of aryl halides with NaCN in the presence of crowned phosphine complexes of palladium under solid-liquid two-phase conditions".
Mowry, Chem. Rev., vol. 42 (1948), pp. 189-283, "The Preparation of Nitriles".
Sundermeier et al., Eur. J. Inorg. Chem. (2003), pp. 3513-3526, "Palladium-catalyzed cyanation of aryl halides . . . ".
Sundermeier et al., Chem. Eur. J., vol. 9 (2003), pp. 1828-1836, "Progress in the palladium-catalyzed cynation of aryl chlorides".
Friedman et al., J. Org. Chem., vol. 26 (1961), pp. 2522-2524, "Dimethylformamide as a useful solvent in preparing nitriles from aryl halides . . . ".
Schareina et al., J. of Organomet. Chem., vol. 689 (2004), pp. 4576-4583, "Improving palladium-catalyzed cyanation of aryl halides . . . ".
Weissman et al., J. Org. Chem., vol. 70 (2005), pp. 1508-1510, "Ligand-free palladium-cataylzed cyanation of aryl halides".
Marcantonio et al., Org. Letters, vol. 6 (2004), pp. 3723-3725, "An investigation into causes and effects of high cyanide levels in the palladium-catalyzed cyanation reaction".
Reetz et al., Chem. Commun. (2004), pp. 1559-1563, "Ligand-free Heck reactions using low Pd-loading".
Chidambaram, Tet. Letters, vol. 45 (2004), pp. 1441-1444, "A robust palladium-catalyzed cyanation procedure: beneficial effect of zinc acetate".
Tschaen et al., Syn. Commun., vol. 24 (1994), pp. 887-890, "An improved procedure for aromatic cyanation".
Takagi et al., Chem. Letters, vol. 5 (1973), pp. 471-474, "Palladium (II) catalyzed synthesis of aryl cyanides from aryl halides".
Merz et al., Chem. Berichte, vol. 10 (1877), pp. 746-765, . . . "Mittheilungen aus dem Universitats-Laboratorium in Zurich".
Takagi et al., Handbook of Organopalladium Chem. for Organic Synthesis, vol. 1 (2002), pp. 657-672, "III.2.13—Palladium-catalyzed cross-coupling involving α-hetero-substituted organometals".

* cited by examiner

*Primary Examiner*—James O Wilson
*Assistant Examiner*—Ebenezer Sackey
(74) *Attorney, Agent, or Firm*—Baerbel R. Brown; Catherine D. Fitch

(57) ABSTRACT

A practical, ligand-free cyanation of aryl bromides employs Pd catalyst in combination with a non-toxic cyanide source, $M_n[Fe(CN)_6]$ (M=K or Na; n is 3 or 4), or a hydrate thereof, and a base. The reactions are performed in a polar aprotic solvents and provide the corresponding aryl nitrile in 83-96% yield, typically in less than 5 h.

17 Claims, No Drawings

CYANATION OF AROMATIC HALIDES

CROSS-REFERENCE TO RELATED APPLICATIONS

This application claims priority of U.S. provisional application Ser. No. 60/627,676, filed Nov. 12, 2004.

BACKGROUND OF THE INVENTION

Aromatic nitriles constitute a key component of numerous commercial compounds including pharmaceuticals, agrochemicals (herbicides, pesticides) and pigments/dyes. For example, *The Merck Index*, Thirteenth Edition, M. J. O'Neil, Ed. 2001, lists 22 compounds that incorporate this functionality. Their utility also stems from the myriad of possible nitrile transformations including the synthesis of benzoic acids/esters, amidines, amides, imidoesters, benzamidines, amines, heterocycles and aldehydes. The traditional method for preparing aromatic nitriles from the corresponding aryl bromides/iodides, Rosemund-Von Braun reaction, requires stoichiometric copper (I) cyanide at elevated temperatures, often with complicated workups. (For a review, see Mowry, D. T. *Chem. Rev.* 1948, 42, 189. (b) for improved conditions, see: Friedman, L.; Shechter, H. *J. Org Chem.* 1961, 26, 2522.) In 1973, Takagi described the first metal-catalyzed cyanation of aryl halides that also happened to be a ligand-free system. (Takagi, K.; Okamoto, T.; Yasumasa, S.; Oka, S. *Chem Letters* 1973, 5, 471-4.) This methodology employed KCN and 2 mole % $Pd(CN)_2$ (for the aryl bromides substrates) with conversions ranging from 64 to 91% at $\geq$140° C. Since then, palladium-based methods have garnered most of the attention due to functional group tolerance, air stability and high catalytic activity but none of these methods offered the ligand-free advantage. (For reviews, see: (a) Sundermeier, M.; Zapf, A.; Beller, M. *Eur. J. Inorg. Chem.* 2003, 3513-3526. (b) Takagi, K., in *Handbook of Organopalladium Chemistry for Organic Synthesis (Ed.: Negishi, E.)*, J. Wiley & Sons: Hoboken, 2002, 1, 657-672.) One constraint of these procedures, which typically use $M^1$—CN ($M^1$=Na, K, TMS, Cu) as the nucleophile, is the high level of dissolved cyanide in the reaction which inhibits the catalytic cycle, namely the oxidative insertion, due to formation of unreactive palladium (II) cyano species. This has led to the use of additives, such as zinc acetate, diamines, zinc dust, $Me_3SnCl$, to enhance the catalytic turnover. (See, Chidambaram, R. *Tet. Letters* 2004, 1441-1444; Sundmeier, M.; Zapf, A.; Mutyala, S.; Baumann, W.; Sans, J.; Weiss, S.; Beller, M. *Chem. Eur. J.* 2003, 9, 1828-1836.; Okano, T.; Iwahara, M.; Kiji, J. *Synlett* 1998, 243; and Yang, C.; Williams, J. M. *Org. Letters* 2004, 6, 2837-2840.) Controlling the CN concentration via defined dosing of the cyanide has also been used towards this end, as has the use of less soluble cyanide reagents such as zinc cyanide and potassium ferrocyanide (II) ($K_4[Fe(CN)_6]$). (For TMS-CN: Sundmeier, M.; Mutyala, S.; Zapf, A.; Spannenberg, A.; Beller, M. *J. Organomet. Chem.* 2003, 684, 50-55. For acetone cyanohydrin: Sundermeier, M.; Zapf, A.; Beller, M. *Angew, Chem. Int. Ed.* 2003, 42, 1661. The use of zinc cyanide in this capacity was introduced by: Tschaen, D. M.; Desmond, R.; King, A. O.; Fortin, M. C.; Pipik, B., King, S.; Verhoeven, T. R. *Synth. Commun.* 1994, 24, 887-890. Also see, Schareina, T.; Zapf, A.; Beller, M. *Chem. Commun.* 2004, 12, 1388; where we observed no need to dehydrate (3 equiv water present) this reagent as was described by the authors in this article. The latter reagent, potassium hexacyanoferrate (II), recently re-discovered as cyanide source by Beller, is particularly intriguing as all six CN are available for reaction, and it is inexpensive, easily handled and non-toxic. The use of ligands was thought to improve the catalytic activity, and allowed for milder reaction conditions and the inclusion of typically unreactive aryl chlorides. The phosphine ligands though are often air/moisture-sensitive, more costly than the palladium species and difficult to remove from the product and to recover. This has led to a re-examination of the role of ligands in Pd-catalyzed aromatic substitution reactions, as evidenced by recent work describing ligand-free Heck, Suzuki, and Sonogashira reactions. ((a) de Vries, A. H. M., Mulders, J. M. C. A., Mommers, J. H. M., Henderickx, H. J. W., de Vries J. G. *Org. Letters* 2003, 5, 3285-3288; Reetz, M. T., de Vries J. G. *Chem. Commun.* 2004, 1559-1563; de Vries J. G., de Vries, A. H. M. *Eur. J. Org. Chem.* 2003, 799; Urgaonkar, S., Verkade, J. G. *J. Org. Chem.* 2004, 69, 5752-5755.) As noted by Beletskaya, "the inherent reactivity of unligated palladium is sufficient for oxidative addition to most kinds of C—X bonds." Beletskaya, I. P; Cheprakov, A. V. *Chem. Rev.* 2000, 100, 3009-3066. This prompted a study into the potential for similar reactivity with the aromatic cyanation reaction. The present invention is directed to a practical, optionally ligand-ree cyanation of aryl bromides using low loadings of ligand-free palladium.

We have developed a practical, ligand-free aryl cyanation methodology utilizing inexpensive, easy-to handle and non-toxic reagents. This procedure gives high yields for a respectable variety of aryl bromides and is amendable to large scale work as the reactions are rapid and require only a modest catalyst charge. This result adds to the growing list of metal-catalyzed reactions that can be performed ligand-free.

SUMMARY OF THE INVENTION

A practical procedure for formation of aryl cyanates (II) from aryl bromides (I):

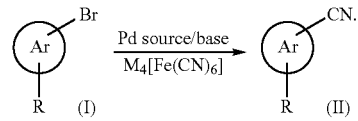

The process of the present invention is a practical, ligand-free aryl cyanation method, which uses inexpensive, easy to handle and non-toxic reagents. The present process provides high yields for a variety of aryl bromides. This process is also amenable to large scale work because, under preferred conditions, the reactions are rapid and require only a modest catalyst charge. The aryl cyanates of formula II are useful in the synthesis of a variety of useful chemical compounds, including compounds of structural formula VI:

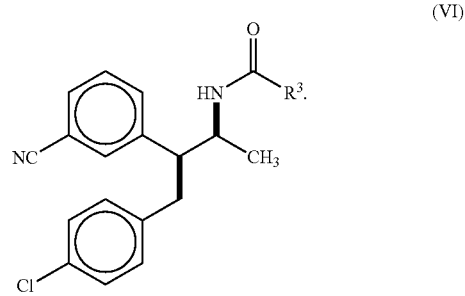

DETAILED DESCRIPTION OF THE INVENTION

The present invention is directed to a process for formation of aryl cyanates (II) from aryl bromides (I):

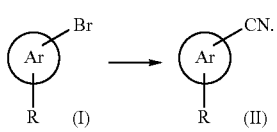

Ar is selected from aryl and heteroaryl, and
R is selected from:
(1) —H, (2)

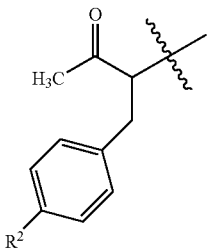

(3) halo,
(4) cyano,
(5) trifluoromethyl,
(6) —$C_{1-3}$ alkyl,
(7) —C(O)—$C_{1-3}$ alkyl,
(8) —$C(O)_2$—$C_{1-3}$ alkyl,
(9) aryl, and
(10) heteroaryl; and
$R^2$ is selected from: hydrogen, halogen and hydroxyl;
comprising treating the bromo compound of formula I with $M_n[Fe(CN)_6]$, or a hydrate thereof, in the presence of a palladium source, and a base in a polar aprotic solvent to form a reaction mixture, wherein: M is selected from sodium and potassium, and n is selected from 3 and 4, and heating the reaction mixture.

In one embodiment of the present invention, Ar is selected from aryl and heteroaryl. In one class of this embodiment, Ar is selected from phenyl, naphthyl, antracenyl, other higher order polyaromatic compounds, pyridyl, and thiophenyl.

In one subclass of this class, Ar is selected from phenyl, naphthyl, and pyridyl.

In another embodiment of the present invention, R is selected from:
(1) —H, (2)

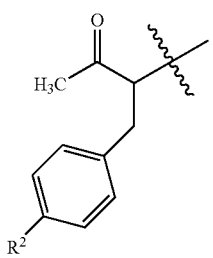

(3) $R^2$
(4) halo,
(5) cyano,
(6) trifluoromethyl,
(7) —$C_{1-3}$ alkyl,
(8) —C(O)—$C_{1-3}$ alkyl,
(9) —$C(O)_2$—$C_{1-3}$ alkyl,
(10) aryl, and
(11) heteroaryl.

In one class of this embodiment, R is selected from:
(1) —H, (2)

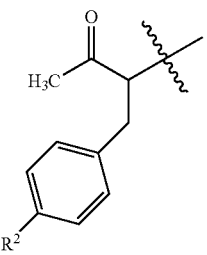

(3) F,
(4) Cl,
(5) cyano,
(6) trifluoromethyl,
(7) methyl,
(8) methylcarbonyl-,
(9) methoxycarbonyl-, and
(10) phenyl.

In one subclass of this class, R is selected from:
(1) —H, (2)

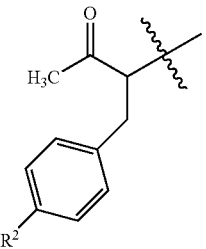

(3) F,
(4) Cl,
(5) cyano,
(6) trifluoromethyl,
(7) methyl,
(8) methylcarbonyl-, and
(9) phenyl.

In another subclass, R is:

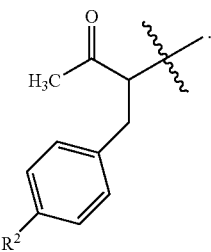

In one embodiment of the present invention, $R^2$ is selected from: hydrogen, halogen and hydroxyl.

In one class of this embodiment, $R^2$ is selected from: hydrogen, fluoro, chloro and hydroxyl.

In one subclass of this class, $R^2$ is chloro.

In one embodiment of the present invention, the palladium source is selected from palladium acetate, tris(dibenzylideneacetone)dipalladium and palladium chloride. In one class of this embodiment, the palladium source is selected from palladium acetate and tris(dibenzylideneacetone)dipalladium. In one subclass of this class, the palladium source is palladium acetate. In one embodiment of the present invention, the palladium source is employed at 0.1 to 0.5 mole % relative to bromo compound I.

In one embodiment of the present invention, the base is selected from metal carbonates, metal bicarbonates, metal phosphates, and nitrogen-based amines. In one class of this embodiment, the base is sodium carbonate. In one embodiment of the present invention, the base is employed at 0.3 to 2.0 equivalents relative to bromo compound I. In one class of this embodiment, the base is employed at about 1.0 equivalent relative to bromo compound I.

In one embodiment of the present invention, the solvent is selected from N-methylpyrrolidinone, dimethylformamide, dimethyl sulfoxide, ethylene carbonate and dimethyl acetate. In one class of this embodiment, the solvent is selected from N-methylpyrrolidinone, dimethylformamide, and dimethyl acetate. In one subclass of this class, the solvent is dimethyl acetate.

In another embodiment of the present invention, the reagent is $M_n[Fe(CN)_6]$, or a hydrate thereof, wherein M is selected from sodium and potassium, and n is selected from 3 and 4. In one class of this embodiment, the reagent is $M_4[Fe(CN)_6]$, or a hydrate thereof, wherein M is selected from sodium and potassium. In yet another embodiment, the reagent is selected from $K_4[Fe(CN)_6]$, $Na_4[Fe(CN)_6]$, and $K_3[Fe(CN)_6]$, and hydrates thereof. In one class of this embodiment, the reagent is selected from $K_4[Fe(CN)_6].10H_2O$, $K_4[Fe(CN)_6].3H_2O$, and $K_4[Fe(CN)_6]$. In a subclass of this class, the reagent is $K_4[Fe(CN)_6].3H_2O$. In one embodiment of the present invention, the $M_n[Fe(CN)_6]$, or a hydrate thereof, is employed at 0.18 to 0.25 mole % relative to the bromo compound I. In one class of this embodiment, the $M_n[Fe(CN)_6]$, or a hydrate thereof, is employed at about 0.22 mole % relative to the bromo compound I.

In one embodiment of the present invention, the process occurs under an inert atmosphere. In one class of this embodiment, the inert atmosphere is selected from nitrogen, and argon. In one subclass of this class, the inert atmosphere is nitrogen.

In one embodiment of the present invention, the solvent mixture is heated to about 90-130° C. In one class of this embodiment, the solvent mixture is heated to about 100-120° C. In one subclass of this class, the solvent mixture is heated to about 120° C.

In one embodiment of the present invention, the process additionally comprises treatment with an amine ligand. In one class of this embodiment, the amine ligand is selected from a secondary monoamine, diamine, or TMEDA. In one subclass of this class, the amine ligand is selected from dicyclohexylamine, DABCO, and TMEDA. In yet another subclass, the amine ligand is DABCO.

In one embodiment of the present invention, the progress of the reaction is monitored by HPLC or TLC. In one class of this embodiment, the reaction is monitored by HPLC.

In another embodiment of the present invention, the reaction mixture is cooled, and the product of formula II is isolated.

One particular embodiment of the present invention involves the formation of compound 2:

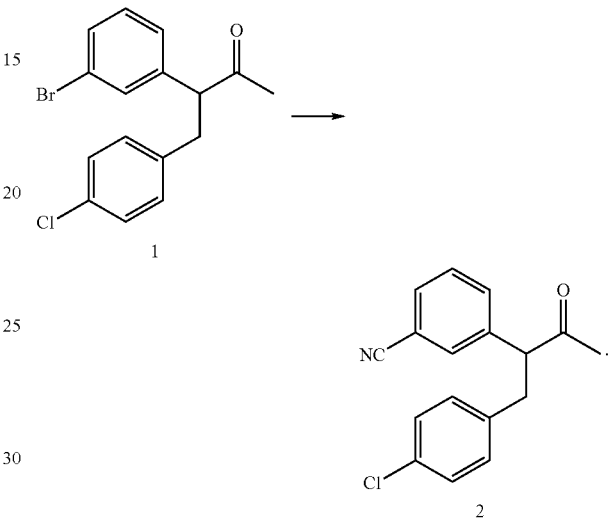

Compound 2 is useful in the syntheses of compounds of structural formula VI:

(VI)

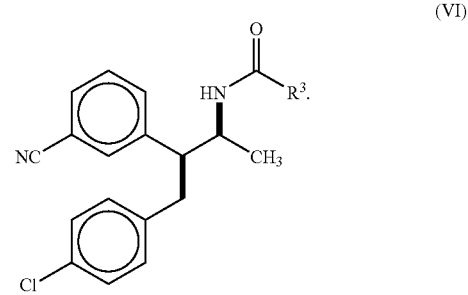

An exemplary synthetic scheme employing an aryl cyanate of the present invention to form a the tosyl compound 3, which is coupled with the primary amide Compound 4, to give the enamide Compound 5, which may be subsequently converted to the pharmaceutically useful Compound 8, N-[1S,2S]-3-(4-chlorophenyl)-2-(3-cyanophenyl)-1-methylpropyl]-2-methyl-2-{[5-(trifluoromethyl pyridin-2-yl)oxy]propanamide, as shown in the scheme below.

Reaction Scheme I:

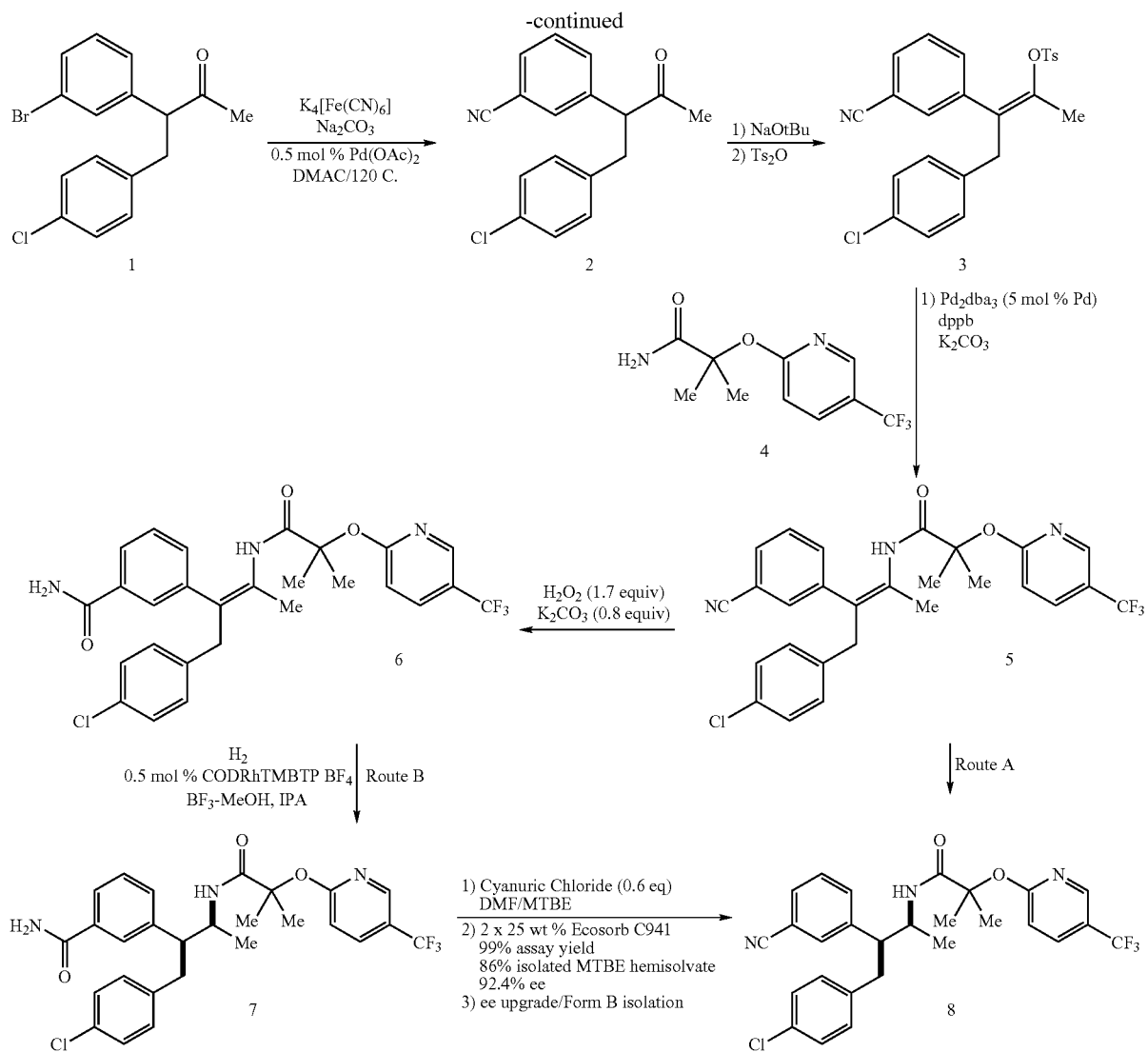

The amide, Compound 4, may be prepared from the corresponding acid, Compound A. Acid Compound A may be made as described in WO 03/077847, or by other means known to the art. The acid, Compound A, may be converted to the amide, Compound 4, by procedures known to those of ordinary skill in the art. One such procedure is treatment with thionyl chloride in an appropriate solvent, in one embodiment an aprotic solvent such as acetonitrile to form the acid chloride followed by treatment with ammonia to form the amide.

The benzonitrile-substituted ketone (2) is formed from the corresponding phenylbromide (1) by treatment with $M_4[Fe(CN)_6]$, wherein M is sodium or potassium in the presence of $Pd(OAc)_2$ catalyst and sodium bicarbonate in a polar aprotic solvent, such as NMP, DMF, or DMAC. In one embodiment of the present reaction, the reaction is conducted under an inert environment, such as nitrogen gas.

The benzonitrile-substituted ketone (2) may be converted to the vinyl tosylate (3) by treatment with a base, such as any alkoxide base, particularly sodium t-butoxide and p-toluenesulfonyl anhydride in a solvent, particularly N,N,-dimethylacetamide, N-methylpyrrolidinone or DMF.

The vinyl tosylate (3) is treated with amide (4) in the presence of base, in particular an inorganic base such as potassium carbonate and a palladium catalyst, particularly tris(dibenzylideneacetone) dipalladium(0), bis(dibenzylideneacetone)palladium(0) and an appropriate phosphine ligand, particularly a diphosphine ligand, such as 1,4-bis(diphenylphosphino)butane or 1,1'-bis(diisopropylphosphino) ferrocene in an appropriate solvent, particularly a tertiary alcohol such as t-amyl alcohol to form the cyano enamide (5).

The cyanoenamide (5) may be either directly stereospecifically reduced to the desired cyano amide (8), (Route A) or it may be first converted to the amide-enamide (6), stereospecifically reduced to the corresponding chiral amide (7), and then converted to the cyano-amide (8) (Route B).

In Route A, the cyanoenamide (5) is treated with hydrogen in the presence of a chiral catalyst to form the desired cyano-amide product (8). The cyanoenamide is dissolved in an appropriate solvent such as methanol, ethanol, isopropanol, trifluoroethanol, THF, isopropyl acetate, ethyl acetate, toluene, methylene chloride, dichloroethane, DMA, DMF, water, or a combination of these solvents, particularly methanol, THF or trichloroethane, and most particularly dichloroethane. The reaction is generally carried out at a concentration of about 5 to 200 g/L solvent, particularly 10 to 100 g/L solvent or 60 to 100 g/L. The hydrogen gas is generally employed at a pressure between 1 and 100 atmospheres, particularly between 20 to 80 atmospheres, more particularly 30 and 60 atmospheres. An additive, such as acetic acid, tetrafluoroboric acid, trifluoroacetic acid, toluene sulfonic acid, methanesulfonic acid, phosphoric acid, citric acid or a Lewis acid such as: $BF_3$.solvent, $B(OMe)_3$, $B(O-iPr)_3$, LiBF4, LiOTf, $NaPF_6$, $Cs_2CO_3$, $MgSO_4$, $Sc(O-iPr)_3$, $Cu(OTf)_2$, $[[Cu(OTf)]_2$.benzene], $Cu(COCF_3)_2$.$H_2O$, $Zn(OTf)_3$, $Sc(OTf)_3$, $La(OTf)_3$, $Mg(OTf)_2$, $LiBF_4(DME)_3$, $K(BPh_4)$, and $BEt_3$, particularly $BF_3$-MeOH, may be optionally employed in the reaction mixture. In one example, no additive is employed. The additive may be favorably employed between 0 and 200 mol %, particularly between 0 and 40 mol %; preferably the additive is not present (0 mol %). The chiral catalyst may be a preformed catalyst complex, in particular, (R,S)-(di-t-butylphosphino)ferrocenyl-ethyldi-3,5-dimethylphenylphosphine (COD)RhBF4, or the chiral catalyst complex may be formed in situ metal precursor, such as (NBD)2RhBF4, a ligand such as (R,S)-(di-t-butylphosphino)ferrocenyl-ethyldi-3,5-dimethylphenylphosphine, (−)-TMBTP, or (R)-Hexaphemp and optionally a catalyst activator, such as tetrafluoroboric acid. The catalyst to substrate molar ratio is from 10 to 500, particularly 20 to 100, most particularly 30 to 50.

In Route B, the cyano-enamide (5) is converted to the corresponding amide-enamide (6), by methods well known to those of ordinary skill in the art. In particular, the cyano-enamide (5) is treated with aqueous hydrogen peroxide in the presence of a base, particularly an inorganic base such as potassium carbonate in an appropriate solvent such as DMSO. The resulting amide-enamide (6) is treated with hydrogen in the presence of a chiral catalyst to form the desired chiral amide product (7). The amide-enamide is dissolved in an appropriate solvent such as methanol, ethanol, isopropanol, trifluoroethanol, THF, isopropyl acetate, ethyl acetate, toluene, methylene chloride, dichloroethane, DMA, DMF, water, or a combination of these solvents, particularly from methanol, ethanol, isopropanol, and trifluoroethanol, and most particularly isopropanol. The reaction is generally carried out at a concentration of about 5 to 200 g amide-enamide (6) per liter solvent, particularly 10 to 100 g/L solvent or 60 to 100 g/L. The hydrogen gas is generally employed at a pressure between 1 and 100 atmospheres, particularly between, more particularly between 20 and 40 atmospheres. An additive, such as acetic acid, tetrafluoroboric acid, trifluoroacetic acid, toluene sulfonic acid, methanesulfonic acid, phosphoric acid, citric acid or a Lewis acid such as: $BF_3$.solvent, $B(OMe)_3$, $B(O-iPr)_3$, LiBF4, LiOTf, $NaPF_6$, $Cs_2CO_3$, $MgSO_4$, $Sc(O-iPr)_3$, $Cu(OTf)_2$, $[[Cu(OTf)]2$-benzene], $Cu(COCF_3)_2$.$H_2O$, $Zn(OTf)_3$, $Sc(OTf)_3$, $La(OTf)_3$, $Mg(OTf)_2$, $LiBF_4(DME)_3$, $K(BPh_4)$, and $BEt_3$, particularly tetrafluoroboric acid, trifluororacetic acid and $BF_3$.MeOH, more particularly $BF_3$.MeOH, may be optionally employed in the reaction mixture. The additive may be favorably employed between 0 and 200 mol %, particularly between 3 and 40 mol %, preferably between 20-40 mol %. The chiral catalyst may be a preformed catalyst complex, in particular (−)-TMBTP(COD)RhBF4, or the chiral catalyst complex may be formed in situ metal precursor, such as is $(COD)_2$RhBF4, a ligand such as (R,S)-(di-t-butylphosphino)ferrocenyl-ethyldi-o-tolylphosphine, (R,S)-(diphenylphosphino)ferrocenyl-ethyldi-t-butylphosphine, (−)-TMBTP, (R)-Hexaphemp, and (R)-xyl-BINAP, particularly tetrafluorooboric acid. and a catalyst activator, such as tetrafluoroboric acid. The catalyst to substrate molar ratio is from 10 to 5000, 200 to 500, most particularly 30 to 50.

Representative experimental procedures utilizing the novel process are detailed below. These procedures are exemplary only and should not be construed as being limitations on the novel process of this invention.

Abbreviations: Ac: acetyl; Acac: acetoacetyl; (COD): cyclooctadiene; DABCO: 1,4-diazabicyclo[2.2.2]octane; DARCO KB-B: tradename for carbon resin; dipf: bis-1,1'-diisopropylphosphino ferrocene; DMAC: dimethylacetamide; DMA: N,N-dimethylacetamide; DME: 1,2-dimethoxyethane; DMF: dimethylformamide; dppb: 1,4-diphenylphosphinobutane; dppf: 1,1-bis(diphenyphosphino)ferrocene; ee: enantiomeric excess; in: inches; IPA: isopropyl alcohol; IPAc: isopropyl acetate; LCAP: liquid chromatography area percent; LHMDS: lithium bis(trimethylsilyl)amide; Me: methyl; MTBE: methyl tert-butyl ether; NBD: norbornadiene; NMP: N,N-dimethylpyrrolidinone; $Pd_2$ $dba_3$: bis-palladium tri(dibenzylidene acetone); RT: room temperature; SOLKA : filter aid; tBu: tertiary butyl; TEA: triethylamine; Tf: trifluoromethylsulfonyl (triflate); THF: tetrahydrofuran; TMBTP: tetramethylbisdiphenylphosphino-thiophene; Ts: p-toluenesulfonyl (tosyl).

PREPARATORY EXAMPLE 1

2-methyl-2-{[5-(trifluoromethyl)pyridin-2-yl]oxy}propanamide

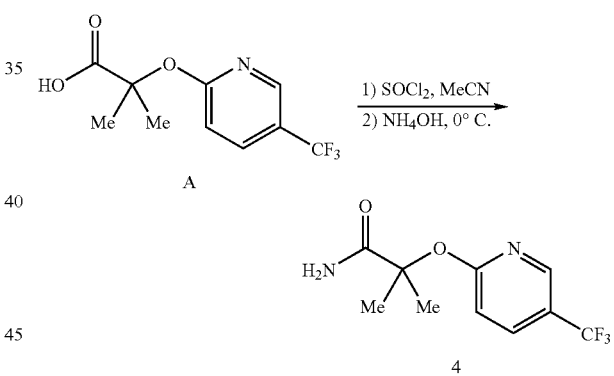

In a 12 L 3-neck separatory funnel equipped with overhead stirrer, nitrogen inlet and thermocouple, a solution of 2-methyl-2-{[5-(trifluoromethyl)pyridin-2-yl]oxy}propanoic acid (772 g) in MeCN (6.5 L) was prepared. Thionyl chloride (316 mol) was added over 30 minutes. The resulting solution was stirred at room temperature for 2 h. A separate 22 L 3-necked round bottom flask equipped with overhead stirrer, nitrogen inlet and thermocouple, was charged with 30% $NH_4OH(aq)$ (5 L) and cooled to −20° C. The acid chloride solution from the separatory funnel was added to the solution of $NH_4OH$ at such a rate that the internal reaction temperature was kept at −15 to −20° C. over 2 h. Once the addition was complete, the resulting slurry was warmed to room temperature and stirred for an additional 1 h. The reaction mixture was transferred to a 50 L extractor containing toluene (15 L) and water (15 L), and the layers were separated. The organic layer was washed with sat'd aq $NaHCO_3$ (5 L), and then with water (5 L). The organic layer was transferred to a 12 L four neck round bottom flask, and concentrated under vacuum at 50° C. to about 2 L volume.

Near the end of the concentration, the solid began to precipitate, and the batch was heated to 78° C. to dissolve all of the solids. Heptane (5 L) was added and the batch was allowed to slowly cool, affording a crystalline solid. The slurry was filtered, and the filter cake was washed with n-heptane (I L). The resulting solid was dried under a stream of nitrogen to afford 626 g of the title compound (99.6 LCAP, 98.0 wt %, 81% isolated yield).

EXAMPLES 1-12

General Considerations: All reactions were carried out in a nitrogen atmosphere. All starting materials (with the exception of the starting material for Example 1), reagents and solvents were obtained from commercial sources and were used without purification. Assay yields were determined using HPLC in comparison to reference standards. All known compounds (entries 2-12) were identified by NMR ($^1$H, $^{13}$C) and were identical to published values (Aldrich Library of NMR Spectra; $2^{nd}$ Edition, 1983).

General Procedure: A 25 mol flask was charged with the aryl bromide (6 mmols), DMAC (10 mol), $K_4[Fe(CN)_6]°3H_2O$ (557 mg; 1.32 mmols; 0.22 eq), sodium carbonate (636 mg; 6 mmols; 1.0 eq) and $Pd(OAc)_2$ (0.1-0.5 mole %; either as a solid or as a 1 mg/mol solution in DMAC). The flask was evacuated and filled with nitrogen (2×) and heated to 120° C. Reaction conversion was monitored by HPLC. Upon completion, the reaction mixture was cooled to RT and diluted with 20 mol EtOAc. The resulting slurry was filtered and the filtrate assayed for content. The product can be isolated by washing the filtrate with water (2×15 ml) and 5% $NH_4OH$ (1×15 mol). The organic layer is dried over $Na_2SO_4$ and the volatiles removed in vacuo to provide the product.

EXAMPLE 1

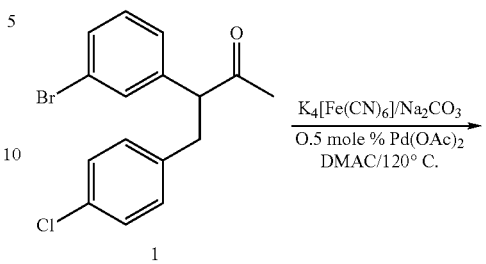

Compound 2: Actual $Pd(OAc)_2$ charge: 0.5 mole %, unoptimized. Sample was purified via recrystallization from toluene/heptane. $^1$H NMR (400.13 MHz, $CDCl_3$): δ 7.57 (td, J=7.2, 1.6 Hz, 1H), 7.48 (m, 1H), 7.44 (t, J=7.2 Hz, 1H), 7.41 (td, J=7.2, 1.6 Hz, 1H), 7.19 (m, 2H), 6.95 (m, 2H), 3.93 (t, J=7.6 Hz), 3.38 (dd, J=14.0, 7.5 Hz, 1H), 2.87 (dd, J=14.0, 7.5 Hz, 1H), 2.06 (s, 3H). $^{13}$C NMR(100.61 MHz): 206.1, 139.4, 136.9, 132.6, 132.3, 132.1, 131.7, 131.2, 130.2, 129.7, 128.5, 118.2, 113.1, 60.5, 37.8, 29.8. Anal. Calcd. For $C_{17}H_{14}ClNO$: C, 71.96; H. 4.97; N, 4.94. Found: C, 71.86; H, 4.99; N, 4.85. mp: 71-72° C.

EXAMPLES 2-12

The yield was determined by LC vs. authentic standard. In Example 4, 0.18 equiv $K_4[Fe(CN)_6]°3H_2O$ was employed. In Example 5, the starting material was 3-bromobenzonitrile.

| EXAMPLE | PRODUCT | Pd(OAc)₂ CHARGE MOLE % | YIELD % | TIME (h) | CONVERSION (A %) |
|---|---|---|---|---|---|
| 2 | 4-F, 4'-CN biphenyl | 0.15 | 96 | 1 | >99 |
| 3 | 4-MeO₂C, 4'-CN biphenyl | 0.1 | 83 | 5 | >99 |
| 4 | 3-Cl, 3'-CN biphenyl | 0.15 | 81 | 3 | >99 |

| EXAMPLE | PRODUCT | Pd(OAc)₂ CHARGE MOLE % | YIELD % | TIME (h) | CONVERSION (A %) |
|---|---|---|---|---|---|
| 5 | NC–C₆H₄–CN (1,3) | 0.5 | 90 | 5 | >99 |
| 6 | F₃C–C₆H₄–CN (1,4) | 0.15 | 90 | 2 | >99 |
| 7 | Ph–C₆H₄–CN (1,4) | 0.3 | 91 | 1 | >99 |
| 8 | C₆H₅–CN | 0.1 | 92 | 1.5 | >99 |
| 9 | Me–C₆H₄–CN (1,4) | 0.1 | 90 | 2 | >99 |
| 10 | 3-cyanopyridine | 0.5 | 86 | 8 | >99 |
| 11 | 1-naphthonitrile | 0.2 | 92 | 1.5 | >99 |
| 12 | Me(O)C–C₆H₄–CN (1,4) | 0.1 | 86 | 5 | 95 |

EXAMPLE 13

3-(4-chlorophenyl)-2-(3-cyanophenyl)-1-methyl-prop-1-en-1-yl 4-methylbenzenesulfonate

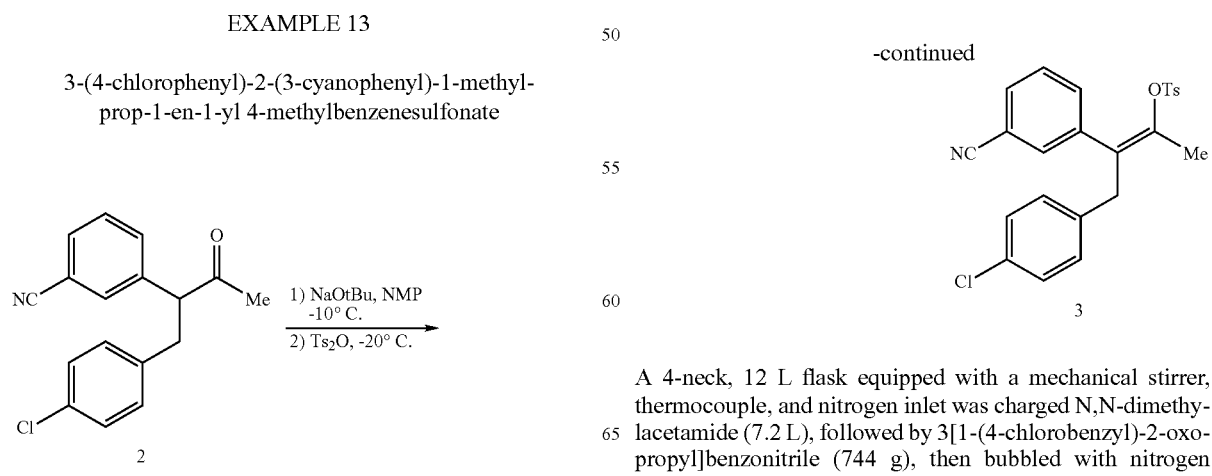

A 4-neck, 12 L flask equipped with a mechanical stirrer, thermocouple, and nitrogen inlet was charged N,N-dimethylacetamide (7.2 L), followed by 3[1-(4-chlorobenzyl)-2-oxopropyl]benzonitrile (744 g), then bubbled with nitrogen through the reaction mixture for 30 minutes at room temperature. (Note: the 3[1-(4-chlorobenzyl)-2-oxopropyl]benzonitrile (744 g) employed in this procedure was made by a procedure different from that in Example 1. The mixture was cooled to −10° C., and NaOtBu (265 g) was added as a solid in one portion with stirring (tmax=−2° C.). The solution was allowed to stir with cooling until the exotherm stopped and the temperature began to drop (approx. 2 minutes). The cooling bath was removed, and the reaction was warmed to room temperature, then stirred for 1 hour. The mixture was cooled to −20° C. and p-toluene sulfonic anhydride (Ts$_2$O, 893 g) was added as a solid in two portions with stirring, keeping the temperature below −5° C. (tmax=−8° C.). The mixture was allowed to cool back to −10° C. and stirred for 1 hour. The reaction was quenched with 1 M NaHCO$_3$ (1.9 L), and transferred to a 50 L extractor containing 15 L IPAc and 13 L water. The layers were separated and the organic layer was washed twice with 7.5 L water. The organic layer was concentrated under slight vacuum (25 in Hg) at 55° C. to −2 L. Upon reaching the 2 L volume, the batch began to crystallize, so the vacuum was turned off and the flask was heated to 73° C. to produce a homogeneous solution. Heptane (6.6 L) was added while the mixture was allowed to slowly cool to room temperature. The resulting slurry was aged for 1 h at room temperature, then filtered. The filter cake is washed with 3 L heptane and dried under a stream of nitrogen to yield 974 g of the title compound (>99 area %, >99 wt %, 85% isolated yield).

EXAMPLE 14

N-[(1 Z)-3-(4-chlorophenyl)-2-(3-cyanophenyl)-1-methylprop-1-en-1-yl]-2-methyl-2-{[5-(trifluoromethyl)pyridin-2-yl]oxy}propanamide

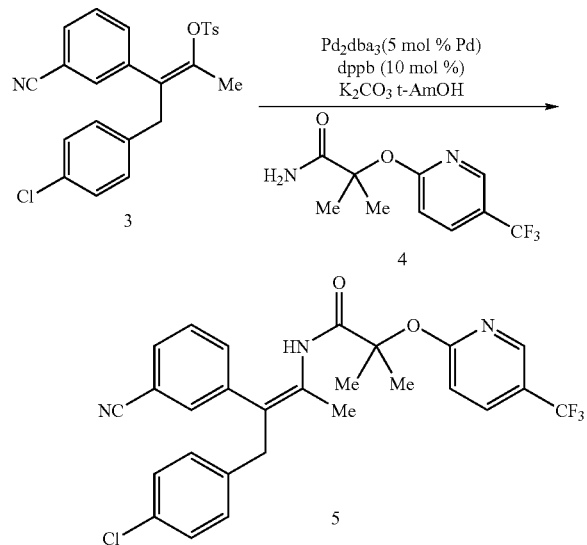

A 3-neck 3 L round bottom flask was charged with tert-amyl alcohol (2.4 L). Nitrogen gas was bubbled through the solution for 2 hours. A 3-neck 5 L round bottom flask fitted with a mechanical stirrer, reflux condenser, and a nitrogen/vacuum adapter on top of the reflux condenser was charged with Pd$_2$dba$_3$ (27.5 g), 1,4-bis(diphenylphosphino)butane (51.2 g), 2-methyl-2{[5-(trifluoromethyl)pyridine-2-yl]oxy}propanamide (313 g), 3-(4-chlorophenyl)-2-(3-cyanophenyl)-1-methylprop-1-en-1-yl 4-methylbenzenesulfonate (526 g), and potassium carbonate (332 g). The flask was sealed, evacuated, and backfilled with nitrogen. Tert-amyl alcohol (2.4 L) was added to the reaction flask followed by heating to 100° C. and stirring at 100° C. for 18 h. The resulting suspension was cooled to 25° C. and transferred into a 4-necked 22 L round bottom flask equipped with a mechanical stirrer. The batch was diluted with 7.2 L of MTBE, then DARCO KB-B® (250 g) was charged to the mixture. The resulting mixture was stirred for 2 h at RT, then filtered over a pad of SOLKA FLOC. The filter cake was washed with 7 L of MTBE. The batch was vacuum transferred to a 4-necked 12 L round bottom flask equipped with an overhead stirrer and thermocouple. The batch was concentrated at 10-20° C. to remove all the MTBE and then at 30-40° C. to reduce the volume of the remaining t-amyl alcohol to ~1.5 L. Heptane (5 L) was added over ~30 minutes and the batch was cooled to 20° C. The filter cake was washed with 2 L of heptane-MTBE (10:1) and dried under a stream of nitrogen to provide 553 g of the title compound.

EXAMPLE 15

3-{(1 Z)-1-(4-chlorobenzyl)-2-[(2-methyl-2-{[5-(trifluoromethyl)pyridin-2-yl]oxy}propanoyl)amino]-prop-1-en-1-yl}benzamide

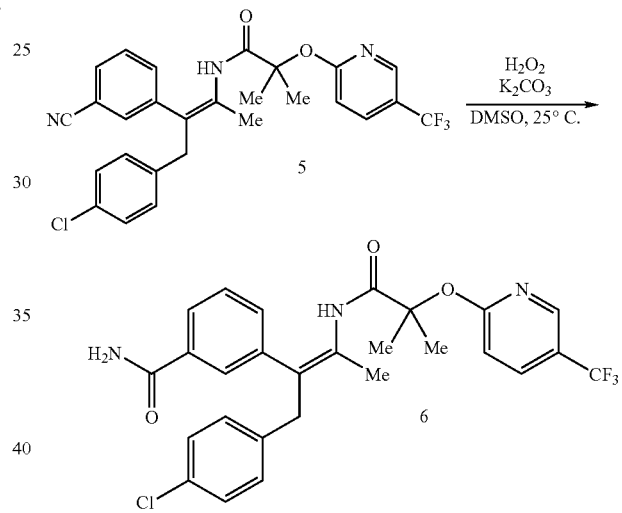

To a 5 L, 3-necked round bottom flask equipped with overhead stirrer, thermocouple, and nitrogen inlet was added 524 g of the cyano enamide product of Example 14, N-[(1Z)-3-(4-chlorophenyl)-2-(3-cyanophenyl)-1-methylprop-1-en-1-yl]-2-methyl-2-{[5-(trifluoromethyl)pyridin-2-yl] oxy}propanamide, and 112 g K$_2$CO$_3$. DMSO (2.7 L) was charged and the vessel was submerged in a RT water bath. Hydrogen peroxide solution (165 mol of a 30% aqueous solution) was slowly added to the reactor such that the temperature never rose above 25° C. After the addition was complete, the reaction was aged for 1 hour. The batch was diluted with 1 L of isopropyl acetate and filtered over a bed of SOLKA FLOC. The bed was washed with 4.5 L of isopropyl acetate and the resulting solution was transferred to a 50 L extractor containing 5.5 L of water. The layers were separated and the organic layer was washed twice with 3.1 L of water, concentrated to 5 L, and solvent switched to 5 L toluene at −60° C. Upon completion of the solvent switch, 500 mol of heptane was added and the mixture was cooled to 20° C. The batch was aged for 30 minutes at 20° C., then filtered and washed with 1 L of toluene. The resulting solid was dried overnight under a stream of nitrogen to afford 522 g of the title compound (99.4 LCAP, 98.0 wt %, 0.02% dppb-oxide, 512 g assay).

EXAMPLE 16

3-{(1S,2S)-1-(4-chlorobenzyl)-2-[(2-methyl-2-{[5-(trifluoromethyl)pyridine-2-yl]oxy}propanoyl)amino]-propyl}benzamide

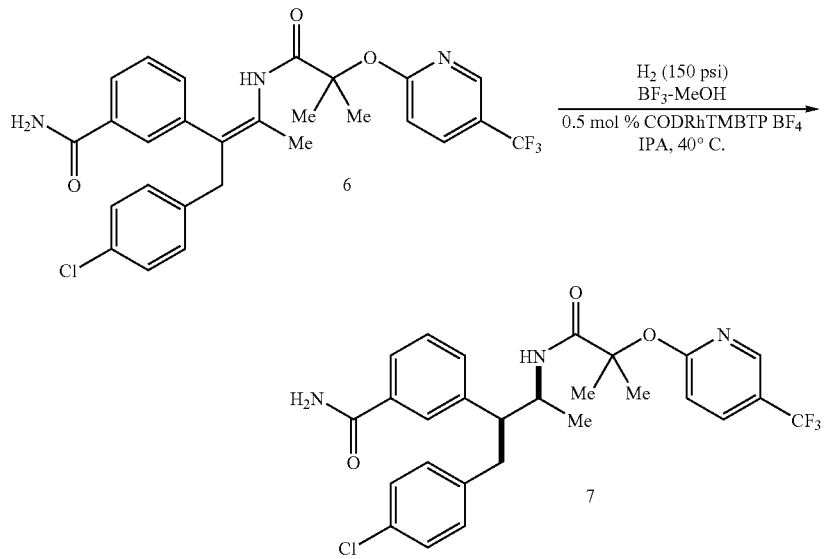

Step A: Catalyst Preparation

In a N$_2$-filled glove box, 2.83 g (−)-TMBTP was added to a 0.5 L bottle containing a stir bar. (COD)$_2$Rh BF$_4$ (1.85 g) was added to the same bottle and then methanol (360 mol) was added. The resulting solution was aged with stirring for 1 hour. BF$_3$-MeOH (41.2 g, 12 wt % in MeOH, 4.94 g BF$_3$) was added to the catalyst solution, and the resulting mixture was added to a 1-L stainless steel bomb. 50 mol of MeOH was used to rinse the mixture into the bomb. Isopropanol (200 mol) was charged to the rinse chamber of the bomb, and then each chamber of the bomb was sealed before removing it from the glove box.

Step B: Hydrogenation

3-{(1Z)-1-(4-chlorobenzyl)-2-[(2-methyl-2-{[5-(trifluoromethyl)pyridin-2-yl]oxy}propanoyl)amino]-prop-1-en-1-yl}benzamide (486 g, Example 15) was charged to a 5 L bottle, and isopropanol (3.3 L) was added to the bottle to create a slurry. The resulting slurry was transferred by vacuum through a polyethylene line into a 2 gallon stainless steel autoclave. The 5-L bottle was rinsed with 1 L of isopropanol and the rinse was also transferred into the 2 gallon autoclave. The autoclave was degassed with N$_2$ (5×), and then placed under partial vacuum. The catalyst bomb was connected to the autoclave via flexible polyethylene tubing (flushed with N$_2$) and the catalyst solution was drawn into the autoclave followed by the isopropanol wash from the rinse chamber. The autoclave was sealed, degassed with N$_2$ purges three times, degassed with H$_2$ purges three times and pressurized up to 150 psi. The stirrer was initiated, and the temperature was raised to 40° C. The reaction was aged at 150 psi, 40° C. for 18 hours. The temperature was dropped to room temperature, and the resulting solution was transferred to a polyethylene jug and assayed for ee and purity (475.7 g assay of the title compound, 98% assay yield, 99.6 LCAP, 92.1% ee).

EXAMPLE 17

N-[1S,2S]-3-(4-chlorophenyl)-2-(3-cyanophenyl)-1-methylpropyl]-2-methyl-2-{[5-(trifluoromethyl pyridin-2-yl)oxy]propanamide: Route B

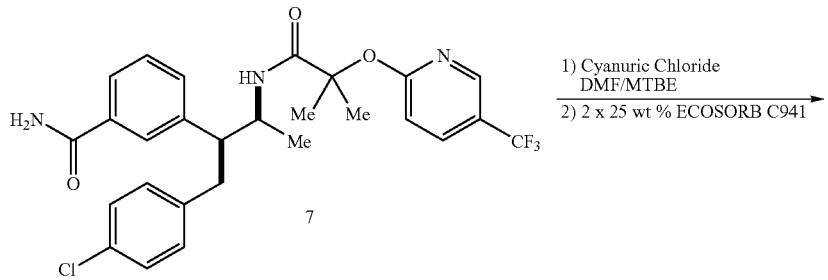

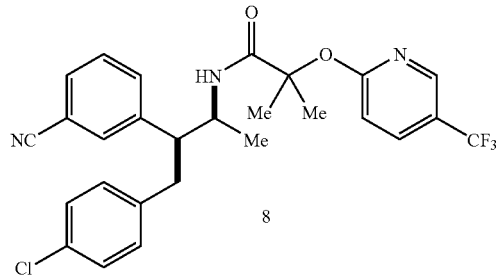

8

The crude hydrogenation solution from Example 16 was solvent switched from 4 L isopropanol to ~1 L DMF (40° C., 30 mm Hg). The resulting solution of 470 g of 3-{(1S,2S)-1-(4-chlorobenzyl)-2-[(2-methyl-2-{[5-(trifluoromethyl)pyridine-2-yl]oxy}propanoyl)amino]-propyl}benzamide (Example 6) in DMF was transferred to a 12 L 4-necked round bottom flask equipped with mechanical stirrer, thermocouple, and 2 L addition funnel. Cyanuric chloride (103 g) was slurried in 2 L of MTBE and the resulting slurry was charged to the reaction via the 2 L addition funnel over ~10 minutes. The reaction mixture was aged with stirring for 1 hour. The batch was cooled to 10° C. and diluted with 3 L of MTBE. 2 L of water and 2 L of saturated $NaHCO_3$ solution were added to the reaction while keeping the temperature below 20° C. The resulting slurry was transferred to a 50 L extractor containing 3 L of MTBE, 3 L of water, and 3 L of sat'd $NaHCO_3$. An additional 12 L of water was added to the batch and the layers were allowed to settle. The organic layer was washed twice with 3 L of water. Assay of the organic layer shows >99% assay yield.

Ecosorb Treatment/Hemisolvate Isolation: The organic layer was azeotroped at 35° C., 17 in Hg to bring the KF to 219 (spec. at 500) while maintaining a volume of ~11 L. The batch was then treated with 320 g of ECOSORB C941. The batch was aged for 4 hours at 50° C., then filtered over a pad of SOLKA FLOC and washed with 6 L of MTBE. The resulting filtrate was recharged to a 22 L vessel, concentrated to 11 L volume, and retreated with 116 g of ECOSORB C941. This slurry was filtered over a bed of SOLKA FLOC, and washed with 6 L MTBE. The resulting colorless MTBE layer was transferred through a 1 micron inline filter into a 12 L, 4 neck round bottom flask equipped with overhead stirrer and thermocouple, and concentrated to ~2 L volume at 17 in Hg, 35° C. The batch was cooled to RT, and a sample was removed to create a seed bed. Once the sample crystallized, it was returned to the flask, and the batch was aged for 30 minutes, creating a large seed bed. The isolated solid was dried over a stream of nitrogen to afford 413.4 g of the title compound as a hemisolvate (92.1% ee, 94.6 wt % title product, 99.8 area %, (0.08 area % methyl ester), 86% isolated yield from 7).

EXAMPLE 18

Isolation of N-[1S,2S]-3-(4-chlorophenyl)-2-(3-cyanophenyl)-1-methylpropyl]-2-methyl-2-{[5-(trifluoromethylpyridin-2-yl)oxyl]propanamide Polymorph B In a 3 L, 3 neck round bottom flask equipped with overhead stirrer and thermocouple, 350 g of N-[1S,2S]-3-(4-chlorophenyl)-2-(3-cyanophenyl)-1-methylpropyl]-2-methyl-2-{[5-(trifluoromethyl pyridin-2-yl)oxy]propanamide hemisolvate was slurried in a total of 1.82 L of 2:3 isopropyl acetate: heptane. The mixture was aged for 1 h, and then filtered over a very small bed of SOLKA FLOC, thoroughly pull the liquors from the filter bed to minimize the loss of mother liquors. The filter cake was washed with 1 L of 1:3 IPAc: heptane into a separate flask. The two filtrates were combined (combined ee=98.5% ee). These two solutions were transferred by vacuum through a 1 micron inline filter into a 22 L 4 neck round bottom flask. The batch was heated to 45° C. over a steam pot, and then charged with 2.35 L of heptane. Seed of N-[1S,2S]-3-(4-chlorophenyl)-2-(3-cyanophenyl)-1-methylpropyl]-2-methyl-2-{[5-(trifluoromethylpyridin-2-yl)oxy]propanamide Polymorph B (Polymorph B seed was obtained from the same solvent system over a long time frame) (15.0 g) was added and the batch was aged at 45° C. overnight. The resulting slurry was then charged with 150 mol of heptane over 5 hours, then 220 mol heptane at 2.0 mol/min, then 1131 mol of heptane at 9 mol/min, then 6783 mol of heptane at 60 mol/min. Once all heptane was charged, the batch was cooled to RT and aged overnight. The batch was cooled to 0° C. and aged for 1 hour, filtered, and washed with 1 L of heptane to afford the title compound, crystal Form B (287 g, 87% isolated yield (from hemisolvate and corrected for seed), 98.6% ee, 99.5 LCAP, 99.5 wt % assay).

EXAMPLE 19

Isolation of 3-{(1S,2S)-1-(4-chlorobenzyl)-2-[(2-methyl-2-{[5-(trifluoromethyl)pyridine-2-yl]oxy}propanoyl)amino]-propyl}benzamide

7

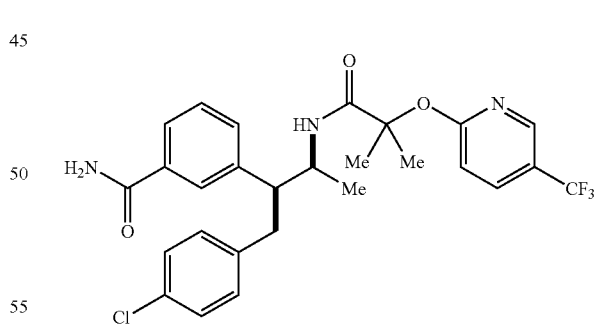

After the hydrogenation was complete (Example 16), solvent was removed on rotovap. The crude oil was diluted with toluene (10 ml/g) and 10% $NH_4Cl$ solution (10 mol/g). The layers were separated, and the toluene layer was concentrated to an oil. The oil was diluted with MTBE (3 mol/g), seeded with 5 wt % chiral amide (7) MTBE hemisolvate and stirred overnight. After a seed bed was generated, heptane (3 mol/g) was added, and the batch was cooled to 10° C. before filtering. 90% recovery of the title product on 3 g scale, 2% in liquors, some stuck to flask. 99.6 LCAP. 0.2% Methyl ester impurity.

EXAMPLE 20

N-[1S,2S]-3-(4-chlorophenyl)-2-(3-cyanophenyl)-1-methylpropyl]-2-methyl-2-{[5-(trifluoromethyl pyridin-2-yl)oxy]propanamide: Route A

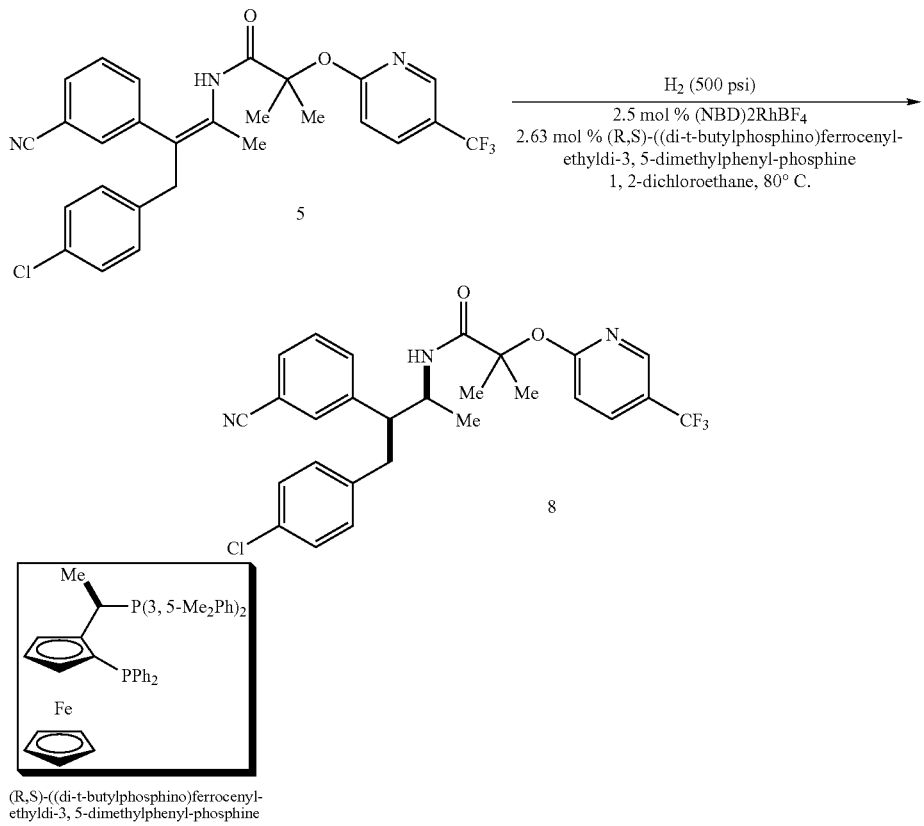

(R,S)-((di-t-butylphosphino)ferrocenyl-ethyldi-3,5-dimethylphenyl-phosphine

Step A: Catalyst Preparation

In a $N_2$-filled glove box, ((R,S)-((di-t-butylphosphino)ferrocenyl-ethyldi-3,5-dimethylphenyl-phosphine), 300 mg) was added to a 30 mol bottle containing a stir bar. $(NBD)_2Rh$ $BF_4$ (183 mg) was added to the same bottle and then 1,2-dichloroethane (20 mol) was added. The resulting solution was aged with stirring for 1 hour, and the resulting mixture was added to a 50 mol stainless steel bomb.

Step B: Hydrogenation

In a $N_2$-filled glove box, starting cyanoenamide (product of Example 4, 10 g) was diluted with 100 mol of 1,2-dichloroethane, and the solution was transferred to a 150 mol stainless steel bomb connected to the 50 mol stainless steel bomb containing the catalyst solution. The 150 mol bomb was connected to the autoclave via flexible polyethylene tubing (flushed with $N_2$) and the substrate solution was drawn into the autoclave followed by the catalyst solution from the upper chamber. The autoclave was sealed and degassed with $N_2$ purges three times. The autoclave was then degassed with $H_2$ purges three times, and pressurized up to 500 psi. The stirrer was initiated, and the temperature was raised to 80° C. The reaction was aged at 500 psi, 80° C. for 18 hours. The temperature was dropped to room temperature, and the resulting solution was transferred to a amber jar and assayed for ee and purity (9.5 g assay of cyanoenamide, 95% assay yield, 90% LCAP, 85% ee).

EXAMPLE 21

3-{(1S,2S)-1-(4-chlorobenzyl)-2-[(2-methyl-2-{[5-(trifluoromethyl)pyridine-2-yl]oxy}propanoyl)amino]-propyl}benzamide: Route B Hydrogenation using ((R,S)-((di-t-butylphosphino)ferrocenyl-ethyldi-o-tolylphosphine)

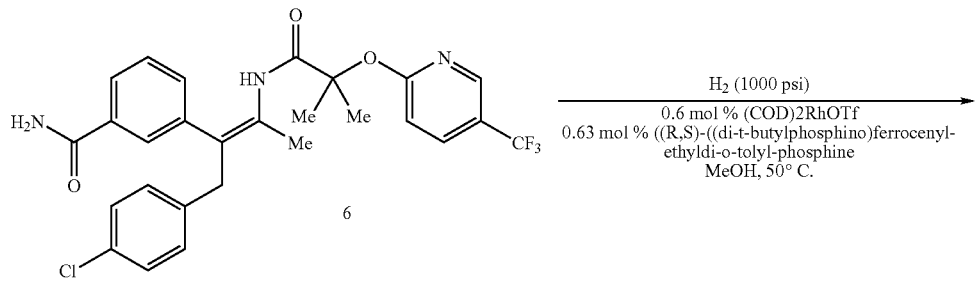

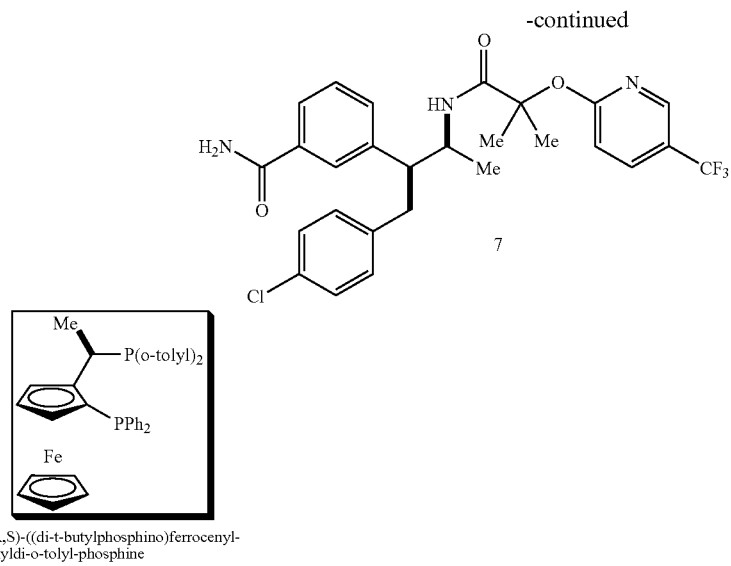

((R,S)-((di-t-butylphosphino)ferrocenyl-ethyldi-o-tolyl-phosphine)

In a $N_2$-filled glove box, (R,S)-((di-t-butylphosphino)ferrocenyl-ethyldi-o-tolylphosphine) (57.1 mg) was added to a 20 mol vial containing a stir bar. $(COD)_2Rh$ OTf (46.8 mg) was added to the same vial and then MeOH (20 mol) was added. The resulting solution was aged with stirring for 20 minutes, and the resulting mixture was added to a 150 mol stainless steel bomb. In a $N_2$-filled glove box, enamide 6 (8.0 g, product of Example 5) was dissolved with 50 mol of MeOH, and the solution was transferred to the same 150 mol stainless steel bomb as the catalyst along with a 10 mol flask rinse. The 150 mol stainless steel bomb was connected to a 25 mol stainless steel rinse bomb containing 10 mol MeOH. The bomb assembly was connected to the autoclave via flexible polyethylene tubing (flushed with $N_2$) and the reaction solution was drawn into the autoclave followed by the MeOH rinse solvent from the upper chamber. The autoclave was sealed and degassed with $N_2$ purges three times. The autoclave was then degassed with $H_2$ purges three times, and pressurized up to 1000 psi. The stirrer was initiated, and the temperature was raised to 50° C. The reaction was aged at 1000 psi, 50° C. for 23.5 hours. The temperature was dropped to room temperature, and the resulting solution was transferred to an amber jar and assayed for ee and purity (98.0% LCAP 7, 92.8% ee 0.2% LCAP enamide 6).

EXAMPLE 22

Isolation of Crystal Type 1 Solvate of 3-{(1S,2S)-1-(4-chlorobenzyl)-2-[(2-methyl-2-{[5-(trifluoromethyl)-pyridine-2-yl]oxy}propanoyl)amino]-propyl}benzamide 3-{(1S,2S)-1-(4-chlorobenzyl)-2-[(2-methyl-2-{[5-(trifluoromethyl)-pyridine-2-yl]oxy}propanoyl)amino]-propyl}benzamide (540 g) was dissolved to a volume of 1.4 L with IPAc. Cyclohexane (1.95 L) was added and the batch was seeded with crystalline hemi-solvate 3-{(1S,2S)-1-(4-chlorobenzyl)-2-[(2-methyl-2-{[5-(trifluoromethyl)-pyridine-2-yl]oxy}propanoyl)amino]-propyl}benzamide (Example 7). After a 20 min age, cyclohexane (13.25 L) was added over 1.5 h. The batch was aged for 1.5 h at RT then cooled to 5° C. with a water-ice bath. The slurry was filtered and washed with cyclohexane (500 mol). The batch was dried in a 35° C. vacuum oven with a nitrogen sweep. ML losses were 48 g (8.8%). The final solid weighed 442.8 g (94 wt % therefore 416 g).

EXAMPLE 23

Isolation of Crystal Type 2 Solvate of 3-{(1S,2S)-1-(4-chlorobenzyl)-2-[(2-methyl-2-{[5-(trifluoromethyl)-pyridine-2-yl]oxy}propanoyl)amino]-propyl}benzamide 3-{(1S,2S)-1-(4-chlorobenzyl)-2-[(2-methyl-2-{[5-(trifluoromethyl)-pyridine-2-yl]oxy}propanoyl) amino]-propyl}benzamide (1012 g) was charged and dissolved to a volume of 4.1 L with MTBE. The batch was seeded with crystalline hemi-solvate 3-{(1S,2S)-1-(4-chlorobenzyl)-2-[(2-methyl-2-{[5-(trifluoromethyl)-pyridine-2-yl] oxy}propanoyl)amino]-propyl}benzamide (Example 7). After a 20 min age, heptane (12.3 L) was added over 1.5 h. The batch was aged for 1.5 h at RT then cooled to 5° C. with a water-ice bath. The slurry was filtered and washed with heptane (2.1 L). The batch was dried in under vacuum with a nitrogen sweep. ML losses were 38 g (3.7%). The final solid weighed 1011 g (93 wt % therefore 940 g).

EXAMPLE 24

Isolation of Crystal Type 3 Solvate of 3-{(1S,2S)-1-(4-chlorobenzyl)-2-[(2-methyl-2-{[5-(trifluoromethyl)-pyridine-2-yl]oxy}propanoyl)amino]-propyl] benzamide Following the bicarbonate treatment as in Example 7, 3-{((S,2S)-1-(4-chlorobenzyl)-2-[(2-methyl-2-{[5-(trifluoromethyl)-pyridine-2-yl]oxy}propanoyl amino]-propyl}benzamide (2.4 g) was dissolved in 80 mol MTBE. Solvent was switched from MTBE to toluene at 35° C. A final volume of ~45 mol was maintained. 15 wt % (0.36 g) of Ecosorb C941 was added and batch aged at 70 to 75° C. Over 90 min. Cooled to rt and filtered over CELITE. The colorless solution was concentrated to dryness and 3 ML (~1.2V) of IPAc was added and kept at 60° C. Then 21 mol of Isooctane was charged over 30 min. Solution was cooled slowly and self seeded at 56° C. (a small amount of the solution is sampled into a vial and cooled to rt to generate the seeds). Once the sample crystallized, it was returned to the batch. Batch became a slurry as it was cooled slowly to rt (over 3 h). Batch was aged at rt over 2 h. A slightly wet solid collected and was left in vac oven to dry overnight at 350° C. Solid HPLC assay gave 99.2 A % and 98 wt %. Chiral HPLC=90.4% ee. NMR results indicate it is an isooctane solvate.

EXAMPLE 25

Analysis of Crystal forms of 3-{(1S,2S)-1-(4-chlorobenzyl)-2-[(2-methyl-2-{[5-(trifluoromethyl)-pyridine-2-yl]oxy}propanoyl)amino]-propyl}benzamide A single crystal was selected for single crystal x-ray data collection on a Bruker Smart Apex system. The unit cell was collected on 30 second scan rate and auto-indexing gave the cell setting to be triclinic. The structure was solved in the triclinic P1 space group after a quadrant data collection using 30 second scan rate.

The X-ray powder diffraction patterns were generated on Philips Analytical X'Pert PRO X-ray Diffraction System with PW3040/60 console. A PW3373/00 ceramic Cu LEF X-ray tube K-Alpha radiation was used as the source. The experiments were run at ambient condition.

In addition to the X-ray powder diffraction patterns, the forms of 3-{(1S,2S)-1-(4-chlorobenzyl)-2-[(2-methyl-2-{[5-(trifluoromethyl)-pyridine-2-yl]oxy}propanoyl)amino]-propyl}benzamide were further characterized by their solid-state carbon-13 and fluorine-19 nuclear magnetic resonance (NMR) spectra. The solid-state carbon-13 NMR spectrum was obtained on a Bruker DSX 400WB NMR system using a Bruker 4 mm double resonance CPMAS probe. The carbon-13 NMR spectrum utilized proton/carbon-13 cross-polarization magic-angle spinning with variable-amplitude cross polarization. The sample was spun at 15.0 kHz. A line broadening of 40 Hz was applied to the spectrum before FT was performed. Chemical shifts are reported on the TMS scale using the carbonyl carbon of glycine (176.03 p.p.m.) as a secondary reference.

The solid-state fluorine-19 NMR spectrum was obtained on a Bruker DSX 400WB NMR system using a Bruker 4 mm CRAMPS probe. The NMR spectrum utilized a simple pulse-acquire pulse program. The samples were spun at 15.0 kHz. A vessel endcap was utilized to minimize fluorine background. A line broadening of 100 Hz was applied to the spectrum before FT was performed. Chemical shifts are reported using poly(tetrafluoroethylene) (teflon) as an external secondary reference which was assigned a chemical shift of −122 ppm.

While the invention has been described and illustrated with reference to certain particular embodiments thereof, those skilled in the art will appreciate that various changes, modifications and substitutions can be made therein without departing from the spirit and scope of the invention. For example, solvents other than the particular solvents as set forth herein above may be useful in the chemical syntheses described herein. It is intended, therefore, that the invention be defined by the scope of the claims which follow and that such claims be interpreted as broadly as is reasonable.

What is claimed is:

1. A process for the synthesis of II,

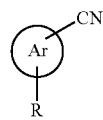

wherein:
Ar is phenyl:
R is:

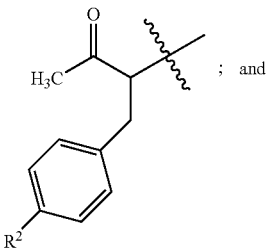

$R^2$ is selected from: hydrogen, halogen and hydroxyl;
comprising treating a bromo compound of formula I:

with $M_n[Fe(CN)_6]$, or a hydrate thereof, in the presence of a palladium source, and a base in a polar aprotic solvent, to form a solvent mixture, wherein: M is selected from sodium and potassium, n is selected from 3 and 4;
and heating the reaction mixture to obtain the product compound II.

2. The process according to claim 1, wherein the product compound II is isolated.

3. The process according to claim 1, wherein the palladium source is selected from palladium acetate, tris(dibenzylideneacetone)dipalladium, and palladium chloride.

4. The process according to claim 3, wherein the palladium source is palladium acetate.

5. The process according to claim 1, wherein the base is sodium carbonate.

6. The process according to claim 5, wherein the solvent is dimethyl acetate.

7. The process according to claim 1, wherein M is potassium, and $M_4[Fe(CN)_6]$ is $K_4[Fe(CN)_6] \cdot 3H_2O$, and is employed at 0.18 to 0.25 mole % relative to bromo compound I.

8. The process according to claim 7, wherein the palladium acetate is employed at 0.1 to 0.5 mole % relative to bromo compound I, and the sodium carbonate is employed at 0.3 to 2.0 mole % relative to bromo compound I.

9. The process according to claim 8, additionally comprising treatment with an amine ligand selected from a secondary monoamine and a diamine.

10. The process according to claim 9, wherein the amine ligand is selected from dicyclohexylamine, DABCO and TMEDA.

11. The process according to claim 10, wherein the amine ligand is DABCO.

12. The process according to claim 1, wherein:
$R^2$ is chloro.

13. The process according to claim 1, wherein the reaction is carried out under an inert atmosphere.

14. The process according to claim 1, additionally comprising treating the compound of formula II with NaOtBu and $[R^4-S(O)_2]_2O$, wherein:

$R^4$ is selected from: aryl, heteroaryl and $C_{1-10}$ alkyl, wherein the aryl and heteroaryl moieties are unsubstituted or substituted with one to three $R^c$ substituents, and the alkyl moiety is unsubstituted or substituted with one or two $R^d$ substituents each $R^c$ is independently selected from halogen, hydroxy, $C_{1-3}$ alkyl, cyano, methoxy and trifluoromethyl;

each $R^d$ is independently selected from: halogen, hydroxy, cyano, methoxy and trifluoromethyl;

to form a compound of structural formula (III):

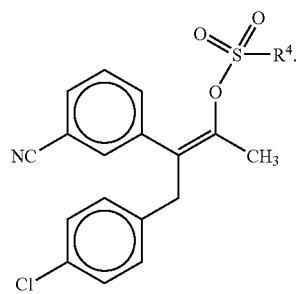

(III)

15. The process according to claim 14, additionally comprising treating the compound of formula III with amide IV:

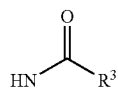

(IV)

in the presence of a base and a palladium catalyst;
wherein:
$R^3$ is

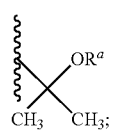

$R^a$ is selected from phenyl, pyridyl, and pyrimidinyl, wherein each of phenyl, pyridyl and pyrimidinyl are independently unsubstituted or substituted with an $R^b$ substituent; each $R^b$ is independently selected from: chloro, iodo, methyl, cyano and trifluoromethyl to form the enamide V:

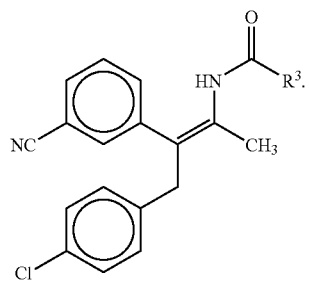

(V)

16. The process according to claim 15, additionally comprising treating the enamide V with hydrogen gas in the presence of a chiral catalyst to form amide VI:

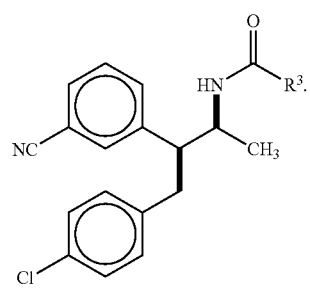

(VI)

17. The process according to claim 16, wherein:
$R^3$ is:

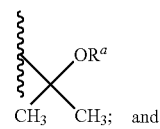

$R^a$ is

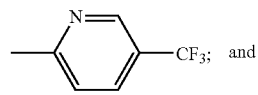

and the hydrogen gas is at a pressure of from 30 to 60 atmospheres.

* * * * *